United States Patent [19]

Shaw et al.

[11] Patent Number: 5,961,832

[45] Date of Patent: Oct. 5, 1999

[54] METHOD AND APPARATUS FOR DIFFUSIVE TRANSFER BETWEEN IMMISCIBLE FLUIDS

[75] Inventors: John Edward Andrew Shaw, West Drayton; Richard Iain Simpson, Hounslow; Adrian James Bull, Manchester; Adrian Mark Simper, Lancaster; Robert George Godfrey Holmes, Preston, all of United Kingdom

[73] Assignee: Central Research Laboratories Limited, Middlesex, United Kingdom

[21] Appl. No.: 08/817,527

[22] PCT Filed: Oct. 20, 1995

[86] PCT No.: PCT/GB95/02488

§ 371 Date: Sep. 16, 1997

§ 102(e) Date: Sep. 16, 1997

[87] PCT Pub. No.: WO96/12540

PCT Pub. Date: May 2, 1996

[30] Foreign Application Priority Data

Oct. 22, 1994 [EP] European Pat. Off. ............... 9421313
Jul. 26, 1995 [EP] European Pat. Off. ............... 9515357

[51] Int. Cl.⁶ .................................................. B01D 11/00
[52] U.S. Cl. ........................... 210/634; 210/85; 210/243; 210/321.84; 210/511; 210/500.26; 210/644; 210/746; 210/748
[58] Field of Search .................................. 210/143, 243, 210/490, 511, 500.26, 634, 748, 222, 223, 695, 643, 644, 321.8, 485, 739, 746, 137; 216/2, 56; 422/101, 69.7; 436/177

[56] References Cited

U.S. PATENT DOCUMENTS 3,956,112  5/1976  Lee et al. ............................. 210/644
4,789,468  12/1988  Sirkar ................................... 210/137
5,039,426  8/1991  Giddings ............................... 210/748
5,043,048  8/1991  Muralidhara ......................... 210/748
5,304,487  4/1994  Wilding et al. ...................... 210/511
5,637,224  6/1997  Sirkar et al. ......................... 210/644
5,707,799  1/1998  Hansmann et al. .................. 422/101

FOREIGN PATENT DOCUMENTS 0246065  11/1987  European Pat. Off. .

OTHER PUBLICATIONS

"Solvent Extraction With Immobilized Interfaces in a Microporous Hydrophobic Membrane", A. Kiani et al., Journal of Membrane Science, 20 (1984) pp. 125–145.

*Primary Examiner*—Joseph W. Drodge
*Attorney, Agent, or Firm*—Evenson, McKeown, Edwards & Lenahan, PLLC

[57] ABSTRACT

In order to facilitate diffusive transfer of an entity such as a solute between immiscible fluids and subsequent separation of the liquids without mixing, a method and an apparatus are disclosed and have first and second flow paths carrying first and second immiscible fluids on opposite sides of a foraminous sheet. The height of the apertures in the sheet is not greater than 200 micrometers (measured perpendicular to the width of the sheet and to the direction of fluid flow), and a stable interface is formed between the fluids within each aperture with a significant amount of fluid flow immediately adjacent the interface. Diffusive transfer takes place across the interface, and subsequently the fluids flow away from the region without mixing. The width of the flow paths measured perpendicular to sheet lies between 10 and 500 micrometers. The walls of each aperture may be parallel or tapered.

30 Claims, 8 Drawing Sheets

METHOD AND APPARATUS FOR DIFFUSIVE TRANSFER BETWEEN IMMISCIBLE FLUIDS

The present invention relates to a method and apparatus for carrying out a process between first and second immiscible fluids, for example mass transfer from one fluid to another.

The use of membranes in liquid/liquid mass transfer processes is known. EP-A-0246065 and Kiani et al, Journal of Membrane Science, 20 (1984) 125–145 "Solvent Extraction with Immobilised Interfaces in a Microporous Hydrophobic Membrane" both disclose the transfer of a solute between two immiscible liquids, wherein the interface between the liquids is defined by a membrane. The mass transfer actually takes place in the pores of the membrane, and a typical membrane used in this process is a Celgard (Registered Trade Mark) 2400 microporous polypropylene film. The membranes are typically of the order of 25 micrometers thick and with an effective pore diameter of 0.02 micrometers. Thus the pores in which the mass transfer takes place are essentially very long and thin. Kiani discloses an hydrophobic membrane. An aqueous phase on one side of the membrane is at a higher pressure than an organic phase on the other side of the membrane and the liquid interface is stabilised on the aqueous side of the membrane.

A problem with such arrangements is that the liquid in the pores at the interface is essentially stationary. With respect to fluid flow on either side of the membrane, the membrane functions as a solid wall so that fluid velocities are essentially zero at the membrane fluid boundaries. This provides unfavourable conditions for interphase transport as the stationary fluid held in the membrane pores extends the distance for diffusion of the transferring entity. Additionally such stagnant regions can accumulate debris and undesirable reaction products which may interfere with inter phase transport of the diffusing solute.

SUMMARY OF THE INVENTION

The present invention is based on the concept of providing for a diffusive transfer process an apertured or foraminous sheet wherein the apertures in the sheet in which fluid interfaces are created between two immiscible fluids on either side of the sheet are such that within either or both fluids flow essentially parallel to the interfaces is continuous up to and at the interface within each aperture and rapid diffusion can take place across the interface.

The present invention provides in a first aspect apparatus for carrying out a diffusive transfer process between first and second immiscible fluids, including first and second fluid flow paths for respective first and second fluids disposed on opposite sides of a foraminous sheet means, wherein an interface between the fluids is formed in use at or in each aperture, characterised in that a minimum height of each of at least the greater part of the apertures, as measured perpendicular both to the direction of fluid flow and to the thickness of the sheet means, is less than 200 micrometers, wherein each aperture has a form such as to permit fluid to flow into the aperture without interfering with fluid flow out of the aperture thereby to permit a significant component of fluid flow immediately adjacent the interface, and wherein outside of the region of the sheet means, the first and second flow paths are separated to permit the respective first and second fluids to flow into and out of said region without mixing.

In a further aspect, the invention provides a method of carrying out a process of diffusive transfer of an entity from a first fluid to a second fluid immiscible with the first, the method comprising:

(1) providing first and second flow paths communicating with one another across a foraminous sheet means, a maximum height of at least the greater part of the apertures in the sheet means being less than 200 micrometers as measured at an interface position in a direction perpendicular both to the direction of fluid flow and to the width of the sheet means, and wherein each aperture has a form such as to permit fluid to flow into the aperture without interfering with fluid flow out of the aperture, (2) flowing the first and second fluids through the respective first and second flow paths such that, at least in the region of the sheet means, the flow of the fluids is essentially laminar and stable interfaces are formed at or in the apertures of the sheet means at said interface positions, with a significant component of fluid flow of each fluid immediately adjacent the interface, (3) permitting diffusive transfer of a significant amount (at least 1%) of the total amount of said entity that may be transferred, and (4) flowing the fluids towards and away from the region of the sheet means in their respective flow paths without mixing of the fluids.

Thus, in accordance with the invention, a method and means are provided for carrying out a diffusive transfer process between two immiscible fluids without creating a risk of mixing of the fluids, while permitting a rapid process of transfer without creating stagnant regions of the fluids at the interface.

The greater the height of the apertures, the more difficult to sustain a stable interface, and in practice heights of greater than 200 micrometers are not useful. It has been found that heights of between 1 and 30 micrometers are preferable. The length of the apertures in the direction of fluid flow are preferably extended for maximum area of interface, and they may be as long as desired.

The sheet means may have apertures all of an essentially uniform size, in which case all apertures fulfill the above dimensional requirements. Where however, the method of formation involves a degree of randomness in the size of the apertures, then in general no single aperture should have a height of more than 200 micrometers and preferably no more than 30 micrometers.

As regards the width of the apertures across the interface, for apertures with inner walls generally normal to the sheet and the interface, then the width of the apertures across the thickness of the sheet and across the interface will be determined by the aspect ratio of width of the aperture to aperture height. In order to enable fluid to flow into the aperture from both sides of the sheet means and to permit a substantial component of fluid flow at the interface, it is in general necessary that the aspect ratio be less than or equal to 1. Thus as aperture height decreases, so must the aperture width and there will in practice be a lower limit determined by the form of the sheet means. If the aspect ratio is greater than one, then fluid flow adjacent the interface is attenuated by reason of the fluid flow into the aperture interfering with fluid flow out of the aperture.

In an alternative form of the apertures, which is of particular relevance where the sheet means is formed as an etched sheet of silicon, the walls of each aperture may have a taper, which may be very wide so that the interface is formed at the narrow end of the aperture or constriction within the aperture, and fluid flows in from the other end of the aperture which may be one or two orders of magnitude wider than the narrow end or constriction. Such a construction may be desirable for ease of manufacture. Such a construction is not subject to the above constraint of aspect ratio being less than or equal to one, since the inflow and outflow of fluid will naturally be separated along the tapered walls at the upstream end and the downstream end of the aperture.

The sheet means may commonly be formed as a planar sheet, although the planar sheet may not necessarily be disposed in a plane but may be formed as a roll or a cylinder. The sheet member may be integral with other structures, for example the walls of fluid flow paths for the first and second fluids.

In some situations, the sheet means may be formed as an integral part of a three dimensional structure. For example, it may be formed as sheet sections extending between larger three dimensional blocks which engage the side walls of fluid flow channels for supporting the sheet sections. As an alternative, and as particularly described in our copending application (PQ12,618) GB-A-2294260, the sheet means may be defined by a thin layer of microspheres, for example, glass which may be fused together so that the spaces between the spheres define the apertures of the sheet means.

In one form, larger spheres packed on either side of the thin layer of small spheres, form a support for the sheet means and provide fluid flow paths for the fluids flowing on either side of the sheet means. As an alternative, the sheet means may be defined by a thin layer of fibres, either woven or nonwoven, which may be fused or otherwise bound together so that the spaces between the fibres define the apertures of the sheet means. In one form, larger fibres packed or woven on either side of the thin layer of small fibres, form a support for the sheet means and provide fluid flow paths for the fluids flowing on either side of the sheet means.

In accordance with the invention, a significant amount of diffusive transfer takes place across the apertures of the sheet means. As is described below, in order for significant diffusive transfer of an entity to take place across the sheet means between the two fluids, there are certain constraints on the width of the fluid flow paths in the interfacial region. It is shown that the width (l) of the first flow path adjacent said interface region and normal to interface is given by the following inequality:

$$l^2 < D.t.x^{-1}$$

Where D is the diffusion coefficient for the first fluid containing the transferring entity to be transferred to the second fluid, t is a time period between 0.1 and 100 seconds for fluid portions occupying a position in the interface regions of the apertures of the sheet means and x is a numerical constant equal to 0.005 or more.

The time t represents the time fluid actually spends in the interface regions of the apertures, and where the apertures are spaced a considerable distance apart within the sheet means, then the total time spent of the fluids in the region of the sheet means will be multiplied by an appropriate scaling factor.

The sheet means may be in the form of a mesh, namely a sheet woven from strands with apertures between the strands. Alternatively the sheet means may be in the form of a perforated foil in which a sheet is perforated in some manner. For example, if the sheet is a silicon sheet the perforations may be formed by etching. Alternatively the sheet means may be formed as a porous membrane from a plastics polymer, providing that the apertures may be made sufficiently large.

Where the apertures are extended in the direction of fluid flow, for maximum area of interface and to aid maintenance of flow at the interface, they may be as long as desired as long as physical stability of the sheet means can be maintained.

One method of formation of sheet members in accordance with the invention is by etching a thin sheet of a silicon or other semiconductor substrate. Clearly other materials such as metals or ceramics may be employed, including silicon nitride or oxide layers which may be supported on silicon substrates. It is possible by etching along a crystal plane, particularly with a silicon substrate to produce apertures with tapered inner walls as described above.

As an alternative, by etching from both sides of the silicon sheet, or by the positioning two etched sheets face to face, it may be arranged that walls tapering in opposite direction meet in the centre of the aperture to give a minimum thickness at the midpoint of the aperture. This is where the interface will preferentially be located and fluids from both side of the sheet means will flow to the narrowed section of the apertures.

The fluids will commonly be liquid, although it is possible that one fluid may be a supercritical fluid or a gas, as long as they are mutually immiscible. For a gas, the gas may be essentially stationary at the interface, since an entity diffusively transferred across the interface will very rapidly diffuse away from the interface in the gas.

In some applications, the liquid on one side of the sheet means according to the invention may be stationary, for example forming a reservoir, or may move intermittently so as to permit a desired level of exchange during the static periods.

Where a process involving three or more fluids is involved, then an appropriate means of carrying out the method may be to provide a stack of at least two spaced sheets, with layers of fluid on each side of each sheet. In this way, parallel processing may be carried out with desired entities diffusing across one or more interfaces between selected fluids.

BRIEF DESCRIPTION OF THE DRAWINGS

Preferred embodiments of the invention will now be described with reference to the accompanying drawings, in which.

DESCRIPTION OF THE INVENTION

Figure 1:
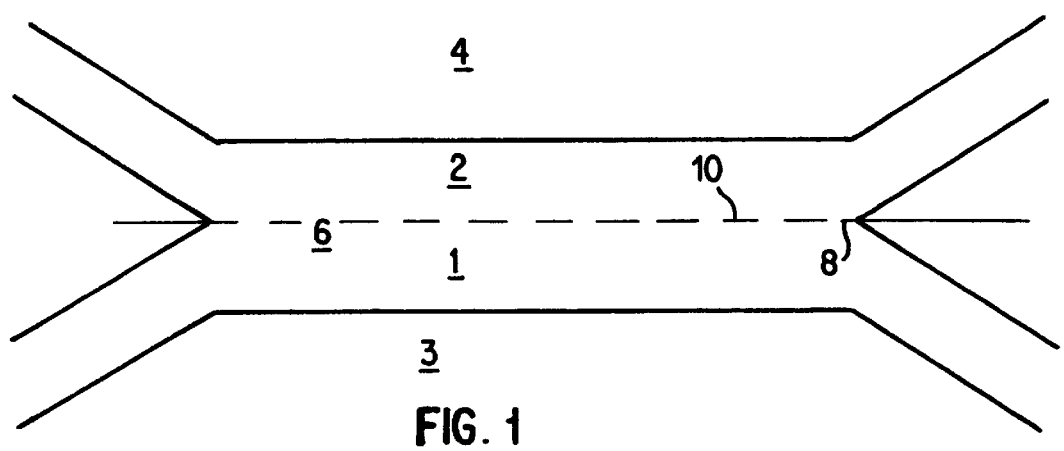
FIG. 1 is a schematic view of a first embodiment of the invention.

Referring now to the first embodiment schematically shown in FIG. 1, two fluid flow paths in the form of channels 1 and 2 are formed as grooves cut, milled or etched in respective solid substrates 3, 4. Each channel in a region 6 communicates with an end surface of the respective substrate. The substrates are positioned against one another with a sheet 8 disposed therebetween, the sheet 8 at least in the region 6 being formed as a foraminous apertured sheet with apertures 10. Sheet 8 is formed from a 20 micrometer thick silicon sheet having circular apertures, 25 micrometers diameter, with their centres 100 micrometers apart. The walls of the apertures are parallel and normal to the sheet.

In use, with mutually immiscible first (aqueous ) and second (organic ) fluids flowing in channels 1 and 2, an interface is defined within sheet 8, with a separate interface region being formed in each aperture of the sheet, across which movement of a desired entity (a metal dissolved in the aqueous phase ) can take place by a process of diffusive transport between the liquids. As a result of the dimensions of the sheet, a substantial component of fluid flow exists within each fluid at the interfaces, giving the advantages set forth above.

The dimensions of channels 1 and 2 in a direction normal to sheet 8 are such that substantial transfer (at least 1% and preferably 50% or more ) of a solute soluble in each of the immiscible fluids between the channels can occur by the process of diffusion to and from the inter-fluid interface within the time it takes the fluids to flow from one end of the sheet to the other. The appropriate values for the width dimension for each fluid flow channel 1, 2 may be determined as follows.

For systems proceeding towards an equilibrium distribution of material by diffusion the progress is a function of diffusion coefficient D of the host fluid, time t, and the geometry and dimensions of the system, which may be represented by a characteristic length l, in the direction of diffusive transport. It can be shown the evolution of diffusion processes may be described in terms of a dimensionless variable $D.t/l^2$, (see. The Mathematics of Diffusion—J. Crank—Second Edition 1975, Oxford University Press). In accordance with the invention, it has been realised that this equation of general application may be employed in determining widths of fluid flow paths or channels.

For significant diffusion to take place in accordance with the invention, there should occur transfer of at least 1%, and preferably 50% or more, of the transferable entity which could be transferred through contact of the fluids for very long periods in the absence of degrading side processes.

If $Dt/l^2>0.01$ transfer will generally amount from 1% to 10% of the maximum at equilibrium, while if $Dt/l^2>0.1$ transfer will be of the order of 50% or more. Thus from the diffusion coefficients of transferring components and the desired transfer times it is possible to determine the appropriate system dimensions. The diffusion coefficients depend on species, medium and temperature, but for small to moderate size molecules in liquid media, the value of D tends to be of the order $10^{-9}$ to $10^{-11}$ m$^2$ s$^{-1}$. Diffusion coefficients in liquid media for high molecular weight species such as some polymers may be substantially lower e.g. $10^{-13}$ m$^2$s$^{-1}$, while coefficients in gases are generally a few orders of magnitude higher. As an example, for rapid (~1 s.) substantial transfer (~50%) of species with diffusion coefficients ~$10^{-10}$ m$^2$ s$^{-1}$, the appropriate length l for the dimension normal to the interfluid interface should be given approximately by substituting the relevant values for D and t into $Dt/l^2$, and equating the expression to 0.1. This example gives l=32 $\mu$m, though in practice dimensions in the range 10 to 100 $\mu$m may be adequate. It may be seen that generally values for appropriate dimensions calculated using the expression $Dt/l^2$ as described for rapid and substantial diffusive transfer will yield average values in the 10 to 500 $\mu$m range for the width dimension in the structures for carrying out transfer between immiscible fluids.

The above expression may be rewritten as, in terms of the embodiment of FIG. 1:

$$l^2<D.t.x^{-1},$$

where x is a numerical constant having the values 0.1, 0.01, or 0.005 or more;

D is the Diffusion coefficient for the transferring entity in the respective first or second fluid;

t is the time the fluid occupies in the vicinity of an interface, and for an apertured sheet, represents the total or integrated time spent adjacent each aperture interface while travelling across the sheet; and l is the width of the respective fluid flow path normal to the interface.

By ensuring that laminar flow conditions prevail in the device, fluctuating pressure differentials across the interface which would be produced by turbulent flows are avoided, so the porous structure can be a thin and relatively open structure. Conventional membranes having pore length to diameter aspect ratios significantly greater than 1, and certainly where the ratio is 10 or greater, are not useful in the present invention. To allow advantageous rapid transfer the sheet thickness must be less than a diffusion distance for the species of interest within the time of transit of the fluid across the sheet. The maximum cross sectional dimensions of the openings are determined by the interfluid interfacial surface tension and the pressure across the interface. A critical dimension is the height of each aperture or opening perpendicular to the direction of fluid flow. Whilst the maximum height for each aperture is 200 micrometers in order to maintain a stable interface within the aperture, it is preferred, for reliability in use and for ease of manufacture, for the height to be between 1 and 30 micrometers.

While in accordance with the well known relationship between maximum pressure differential and the cross sectional dimensions and minimised diameterse, the interface stability may be maximised by use of cylindrical apertures, interfacial transfer between fluids will be enhanced by maximising the open area, and by allowing flow within the fluids to be continuous up to and at the interface. The later conditions may be best met by openings which are not of circular cross section, and especially where the openings are extended in the direction of flow.

In order to enhance the physical stability of the sheet and maintain flow within the fluids up to the interface, the apertures may be constructed so as to show a tapering profile from either or both of the fluid channels towards the interface. This will allow particularly small aperture widths to be achieved with quite abrupt changes in dimensions at the interface aiding pinning of the interface. This situation is shown in FIGS. 4a–f and 5a and 5b which show various configurations of tapered profiles. It will be understood that in the tapered profiles shown in FIGS. 4a–f and 5a and 5b, the interface will lie naturally at the tapered end of the aperture at the sharp discontinuity theredefined.

Referring to FIG. 4, the various views are of apertures formed by an anisotropic etch through a sheet of silicon in a crystal plane with the walls of the etch being defined by the plane. The direction of fluid flow is out of the page. Thus FIG. 4a discloses a 400 micrometer wide silicon sheet 40 with an aperture 42 having walls 44 which taper at an angle of about 55° with the sheet surface. This results in one end of the aperture 46 having a height perpendicular to fluid flow at the interface position of 50 micrometers and the other end of the aperture 48 having a height of 610 micrometers.

Figure 4A:
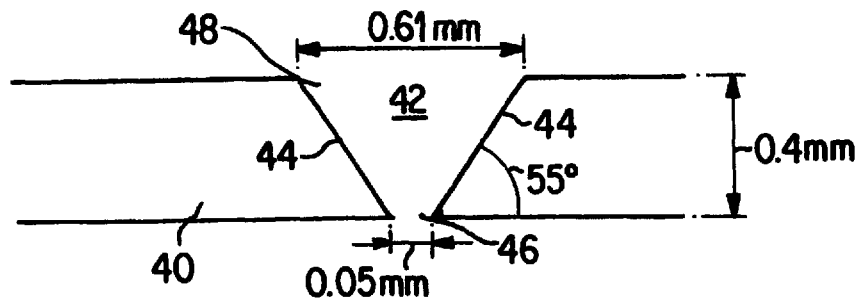
FIGS. 4a–f, 5a and b and 6a–c are schematic views of forms of construction of an aperture in a foraminous sheet of the invention.
Figure 4B:
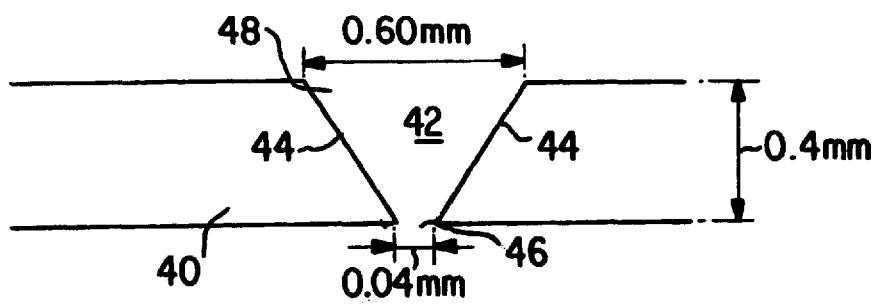
Figure 4C:
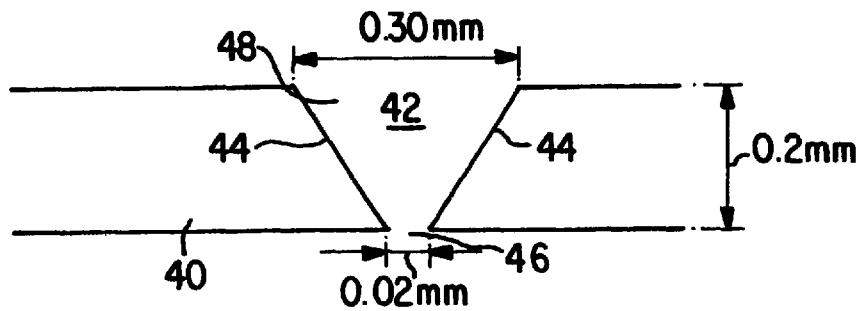

FIG. 4b and FIG. 4c show similar configurations with slightly different dimensions as indicated.

Figure 4D:
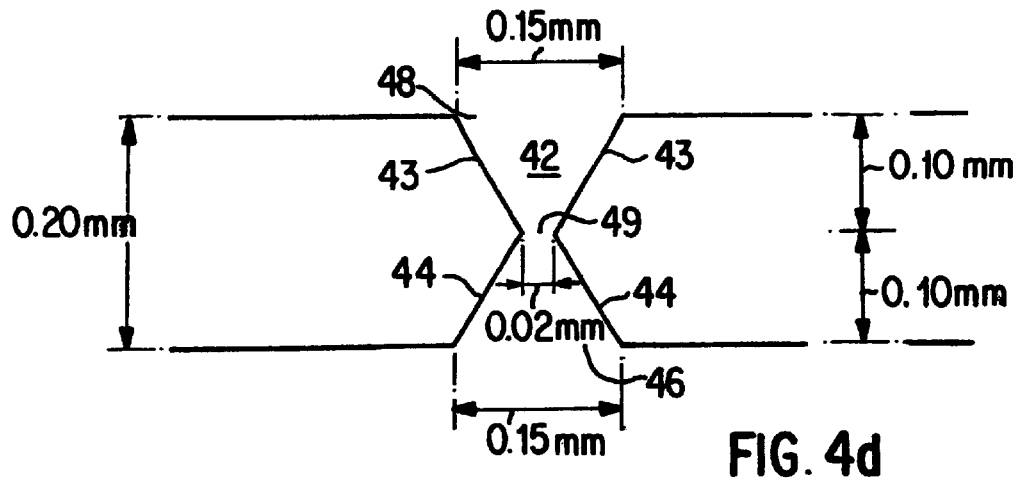

FIG. 4d shows an arrangement wherein the silicon sheet is etched from opposite faces in order to give a waisted cross section for aperture 42. Walls 43 taper inwardly from the upper end 48 of the aperture, 150 micrometers in height perpendicular to fluid flow, and walls 44 taper inwardly from the lower end 46 of the aperture, 150 micrometers in height. At the mid point of the aperture there is a narrow section 49 of 20 micrometers height. In this arrangement, an interface between two immiscible fluids on either side of the sheet will naturally form in narrow section 49.

Figure 4E:
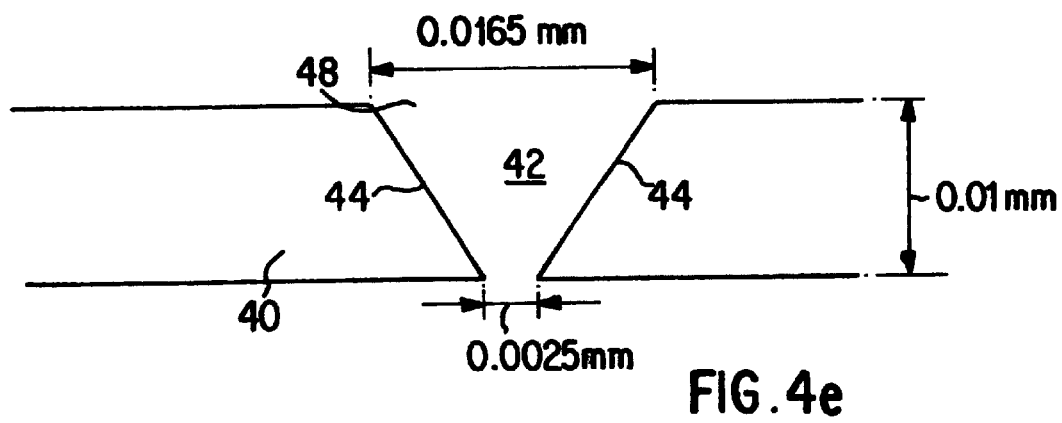
Figure 4F:
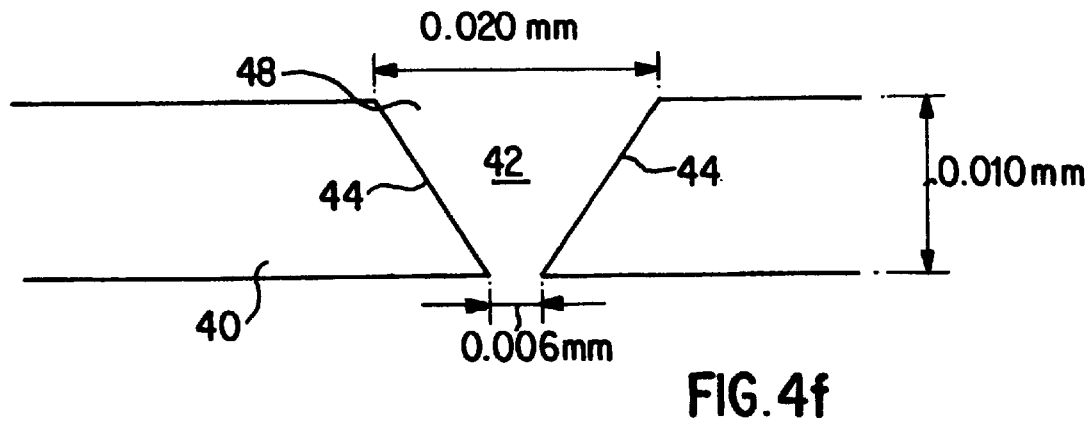

FIGS. 4e and 4f show sections of silicon sheets which may be employed either alone or superimposed with similar sheets to form the arrangement of FIG. 4d. The dimensions for these sheets are indicated in the Figure and it may be seen the sheets are very much smaller in dimension than those in the preceding views.

Figure 5A:
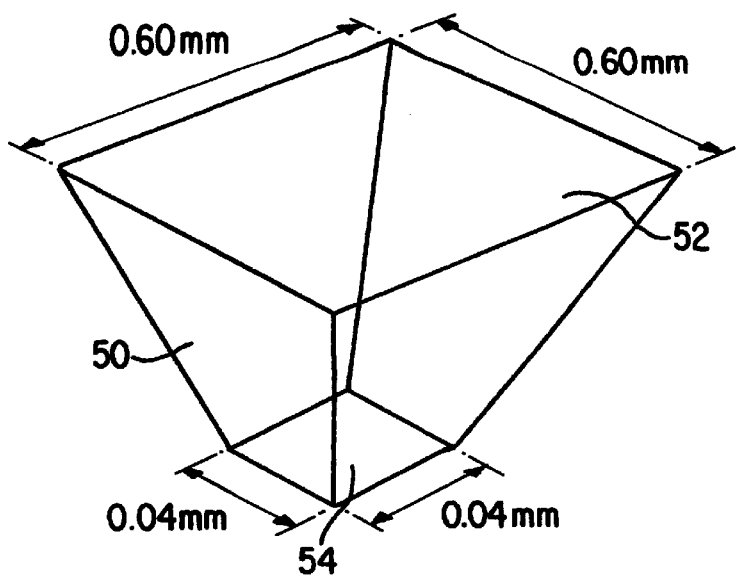

FIG. 5, FIG. 5a is a schematic 3 dimensional view of an aperture 50 formed by etching in a silicon sheet wherein the aperture is of generally rectangular configuration with one end 52 of the aperture being formed as a rectangle with sides of 600 micrometers. The silicon sheet is 400 micrometers thick and with tapered walls extending at an angle of 55°, the end of the aperture 54 at the other face of the silicon sheet is that of a rectangle with sides 40 micrometers wide. Thus the height of the aperture at the interface position 54, perpendicular to fluid flow across the face of the aperture, is 50 micrometers.

Figure 5B:
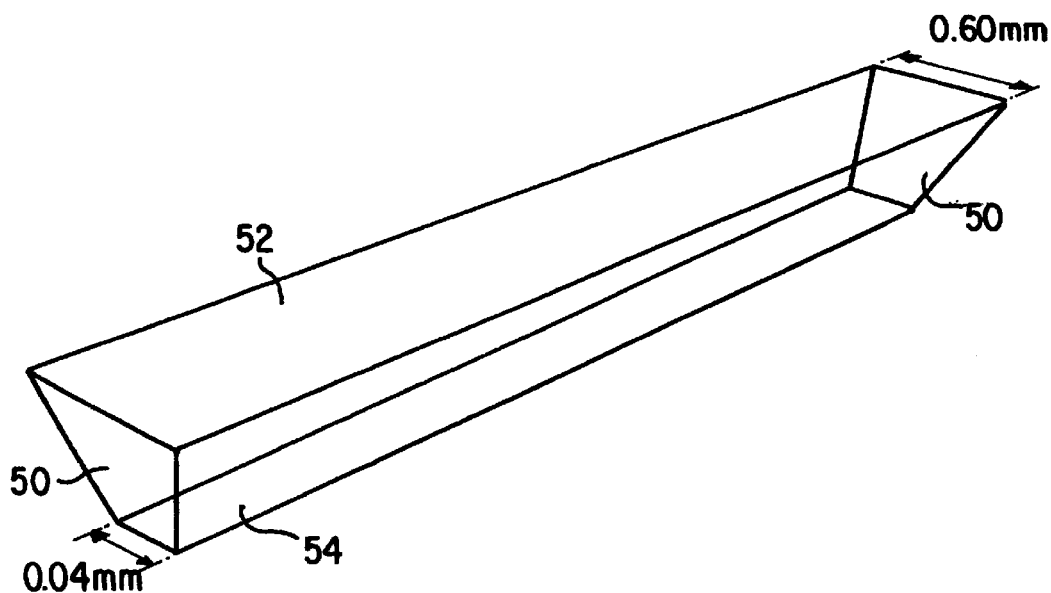

In FIG. 5b a configuration is shown somewhat similar to that in FIG. 5a but which is extended in one dimension parallel to the direction of intended fluid flow the height of the apertures at the interface position normal to fluid flow remains 50 micrometers. The length of the aperture in this dimension may be as long as desired and is subject only to the constraint that the resulting silicon sheet should not be structurally weakened to the point where excessive flexure is caused. It may be seen that the tapered walls 50 at the upstream and downstream end are instrumental in separating the inflow and outflow of the liquid into the aperture, and thus release the dimensions of the aperture from the above-mentioned aspect ratio constraint. The tapered sides 50 parallel to fluid flow prevent any restriction in fluid flow caused by viscous drag along the side walls.

Figure 6A:
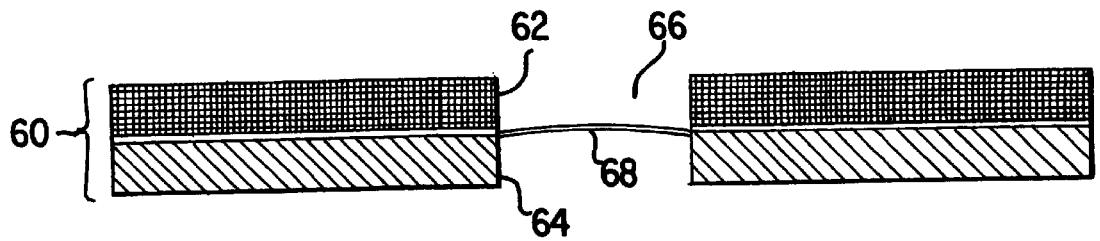
Figure 6B:
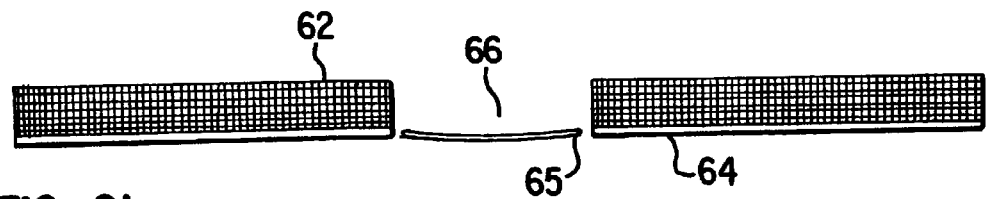
Figure 6C:
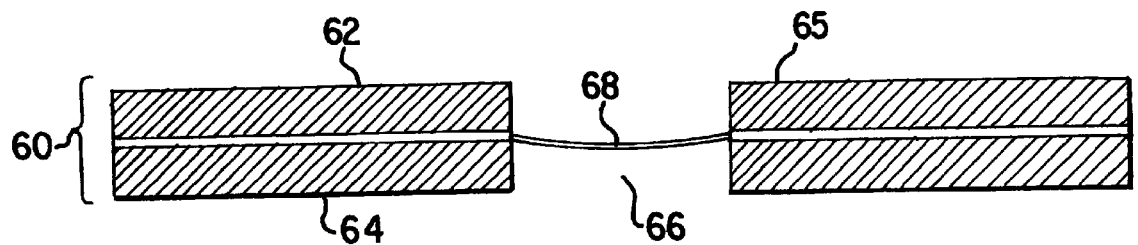

Referring to FIG. 6a–c those various configurations of hydrophobic and hydrophilic surfaces for providing, as described below with reference to FIG. 2, the stability of the interface between immiscible fluids.

In FIG. 6a a foraminous sheet 60 comprises of two layers 62, 64 of metal and polymer, or metal and ceramic and glass, placed together or bonded or in some manner laminated together, layer 62 being of a hydrophilic substance whereas layer 64 is of a hydrophobic substance. Apertures 66 are defined in the sheet 60 and an interface between the two fluids will naturally be located at the junction between the two materials as at 68. The dimensions of the apertures are as indicated above with reference to FIG. 1.

Such dual surface type sheets can alternatively be produced by suitable treatment or coating of one surface of a conventional membrane, e.g. by corona discharge on one surface of a hydrophobic polymer membrane. Thus, in an alternative arrangement as indicated in FIG. 6b, a sheet of hydrophilic material 62 is provided having on one surface a layer of a hydrophobic material 64 deposited in some manner. In this arrangement, an interface between the two immiscible fluids will naturally be formed at the end 65 adjacent surface 64 of the aperture 66.

In the arrangement of FIG. 6c, a foraminous sheet 60 has first and third layers 62, 64 with a second layer 65 which may be of a very thin and fragile material having different surface properties to that of layer 62 and 64 (which may be both of hydrophobic or hydrophilic substances). In this arrangement an interface is naturally formed at the junction with thin layer 65 as at 68 in the aperture 66.

The arrangement shown in FIGS. 6a–c with hydrophobic/hydrophilic surfaces provides for improved stability of interface, as will now be explained with reference to FIG. 2. Similarly the tapered configuration of FIGS. 4a–f and 5a and 5b improves interface stability by reason of the interface being located at a dimensional discontinuity, as will be explained with reference to FIG. 3.

Figure 2:
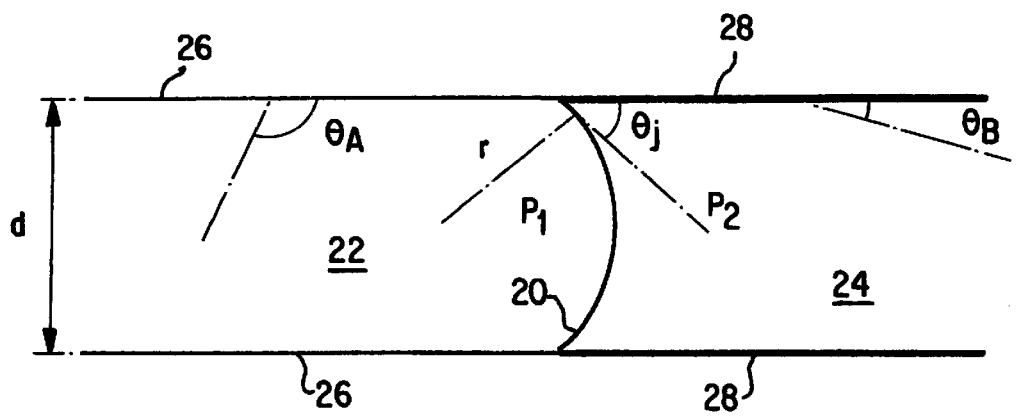
FIGS. 2 and 3 are diagrams illustrating considerations in forming a stable interface between two immiscible fluids.

FIG. 2 represents a cross-section through the interface 20 of two liquids 22, 24 flowing perpendicular to the plane of the paper and confined by parallel walls where the wall material or surface 26, 28 is different either side of the desired interface position 20 (for example hydrophilic/hydrophobic). In FIG. 2, the two liquids have pressures $P_1$ and $P_2$ respectively, and the interface 20 has a radius of curvature r. The difference in pressure $\Delta P=(P_1-P_2)$ is inversely proportional to the radius of curvature and for an interface between the two liquids which is elongated in the direction of flow can be represented as $$\Delta P=\gamma/r,$$

where $\gamma$ is the interfacial tension for the two fluids.

For the situation shown in FIGS. 4a to 6c, where the interface is formed in an aperture bounded on all sides, the above equation may be stated more generally:

$$\Delta P=\gamma/(r_1+r_2),$$

for two radii of curvature in perpendicular directions.

In addition it may be shown that, for the situation of FIG. 2, the condition for a static interface between the two fluids confined between walls at separation d, and where the equilibrium contact angle between the fluid interface and the wall material is $\theta$, is as follows $$\Delta P=(2 \cos \theta)/\gamma d$$

Thus a single value only of pressure differential $\Delta P$ exists for which the interface will be immobile if the wall separation d and contact angle $\theta$ are fixed at single values. Under such conditions it becomes very difficult to fix the interface position at any desired location. In practice hysteresis in the value of the contact angle for real systems can tend to cause the interface to become fixed in position, though not generally where most desired.

Referring to FIG. 2, the equilibrium contact angles for the two fluids with surfaces 26 and 28 are represented by $\theta_A$ and $\theta_B$. Between surfaces of material 26 (left of interface position shown in FIG. 2), an interface will move unless the pressure differential is $\Delta P_A=(2 \cos \theta_A)/\gamma d$. Similar between surface of material 28 an interface will be mobile for all pressure differential except $\Delta P_B=(2 \cos \theta_B)/\gamma d$. However at the junction between materials 26 and 28, there will be a change in contact angle, so that an interval of contact angle and pressure differentials will exist for which the interface to solid surface contact position will not change. This pinning condition will be met while the contact angle at the junction of surface types $\theta j$ lies between $\theta_A$ and $\theta_B$ which corresponds to a finite pressure differential interval. Thus a pinned interface will exist while the pressure differential across the interface $P_1-P_2$ satisfies the expression $$\Delta P_A<(P_1-P_2)<\Delta P_B,$$

In many cases in practice for a sheet with apertures therein as shown in FIG. 2, the interface will be stabilised at one-surface of the barrier. In this situation one phase fills the apertures of the barrier, but is stopped from wetting its outermost surface by the excess pressure exerted by the second phase. This situation may be somewhat limiting as it requires that in use only a fraction of the pressure differential range defined for stability by the aperture dimensions, which applies in both directions through an opening, can in practice be used. For example take the situation where the organic phase preferentially wets the porous barrier and has a higher viscosity than the aqueous phase. In this case the aqueous phase needs to be operated at a higher pressure to stop the organic phase wetting through the barrier. However dependent on channel dimensions in order to achieve the same flow rates for the two phases, the organic phase may need in some regions to be operated at a higher pressures than the aqueous phase to allow for its greater viscosity. Thus a conflict in the required operating parameters can arise. Although this particular problem could be overcome by selecting a barrier which is preferentially wetted by the aqueous phase, there may be problems in selecting suitable materials, and in some circumstances, especially where there is substantial interphase material transfer the direction of pressure differentials and the preferred sheet type may differ from one area of the contactor to another. In this case an improvement will be, as shown in FIG. 6a–c, to form or treat the sheet barrier to make it hydrophilic on one side, so that it is preferentially wetted by the aqueous phase, and hydrophobic on the other side, so that is preferentially wetted by the nonaqueous phase. This will enhance interface stability by locating the interfluid interface at the junction between the two surface types, providing the maximum range of interfacial pressure differential for any chosen aperture dimensions.

Figure 3:
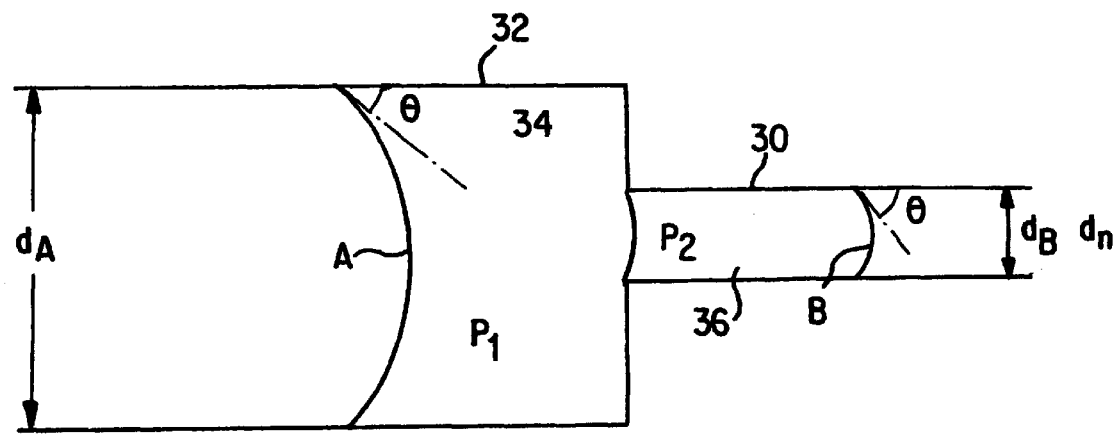

Referring to FIG. 3, this shows the effect of a dimensional discontinuity (Cf. FIGS. 4a to 5b) on interface stability. FIG. 3 represents a cross-section through a junction between two channels 30, 32 of different widths $d_A$, $d_B$ where all walls are taken as being the same material and the equilibrium contact angle $\theta$ does not vary, pressure differentials $\Delta P_A$ and $\Delta P_B$ of fluids 34, 36 denote the single values for immobility in the wide and narrow sections. At the entry to the narrow section a pressure interval for pinning exists given by:

$$\Delta P_A = (2\cos\theta)/\gamma d_A < (P_1-P_2) < \Delta P_B = (2\cos\theta)/\gamma d_B$$

The conditions defined in FIG. 3 and the above formulae for two parallel flows will also apply at the entrance to apertures into a membrane, except that for circular apertures the pressure differential for immobility $\Delta P_B = 2\gamma d_B/(2\cos\theta)$.

Thus it may be seen for the arrangements of FIGS. 4 and 5, the interface at the narrow end of the tapered apertures will be stable for a range of pressure differentials.

There may be situations where the presence of electric fields within or across a foraminous sheet as described above might be advantageous in terms of improving ion transport, electrochemically modifying the transporting species e.g. changing oxidation state of exchanging metal ions, or changing the properties of the interface. With the current invention the sheet may consist of, or incorporate an electronic conductor for example in a mesh including metal or carbon fibres, or be in the form of a perforated foil of such conductors alone or coated or laminated onto a non conductive sheet material. Where the conductor is confined as a layer between two non conductive layers, then electrochemical actions may be confined within the apertures very close to the interface.

To allow an electrochemical bias to be applied to all or part of a foraminous sheet incorporating or formed from electronic conductors, the apparatus used incorporates separate counter and/or reference electrodes. Tonically conducting components must link the foraminous sheet electrodes, and counter and/or reference electrodes, and these will most generally include one or more of the immiscible fluids, especially aqueous solutions. Ionically conducting solids, especially ionically conducting polymers may be incorporated in the apparatus, and may form part of the foraminous sheet, and may link separate electrically conductive elements, one or more of which may be part of the foraminous sheet. The counter or reference electrodes may be positioned as structures such as wires or meshes within one or more of the immiscible fluids, as long as such fluids are ionically conductive and contact the foraminous sheet electrode, or may form part of or be incorporated in the walls of the channels through which such liquids flow, or in additional linked channels containing ionically conducting fluid which need not be flowing. A foraminous sheet may have a composite construction consisting of separate electronically conducting perforated members electronically isolated from each other by an electronically non conducting component which may consist of perforated or porous insulator or ionically conducting material which may contain one or more of the fluids contacting the foraminous sheet.

The electrode systems may be use to carry out a variety of functions affecting the operation of the apparatus. These include:

Changing the redox state of solutes thereby affecting the partition coefficient for solutes between the immiscible fluid phases Changing local acid or alkali concentrations, affecting the speciation of solutes and hence their partition between the immiscible fluid phases, or their mobility within those phases and across the interface.

Changing the electrochemical state of the foraminous sheet surface, and hence its wetting properties, controlling or producing changes in the position of the interfluid interface, thereby affecting the efficiency of solute transfer.

Providing bias across the interfluid interface affecting the kinetics and selectivity of interphase solute transfer.

Changing the rate of transport of solute to and from the interface by providing the driving force for ionic migration to act on the solute species in addition to the diffusive processes operating in the absence of applied electrical bias.

Enabling the modification of fluid flow by electro-osmotic processes.

Providing means for sensing the concentrations of electrochemically active species within the fluid flows, and means for electrochemical titration of species.

Providing the means for in situ cleaning of the components within the apparatus including the foraminous sheet, foraminous sheet apertures, channels, and channel surfaces by electrochemical modification, removal, or destruction of contaminating species or degradation products by redox reactions, changes in surface wetting/adhesion properties, by generating chemically active species to react with and remove contaminants or degradation products, by generating gas bubbles to physically disturb and move contaminants or degradation products.

Where the electronically conductive component covers or forms one or more surface of the foraminous sheet contacting an ionically conducting fluid, it may be used to carry out processes affecting the fluid throughout the laminar flow channel adjacent to the electrode, such as progressive change in redox condition of species throughout that flow. Alternatively it may be desirable that electrochemical action is confined to the interfluid interface region within the apertures. This may be achieved for example by providing for the electronically conducting phase to contact ionically conductive fluid only within the apertures by use of a composite structure for the foraminous sheet whereby non conducting material with apertures continuous with those in the conductor forms part of the foraminous sheet preventing contact between electronic and ionic conductors except within the pores or apertures. Such a non conducting layer may be on one side of the foraminous sheet only if the fluid on the other side does not have ionically conductive properties, or may be on both sides of the electronically conductive layer so that all foraminous sheet electrode to fluid contacts are confined to the periphery of the apertures or pores. An advantage of foraminous sheets where electrochemical action is confined to the pores adjacent to the interfluid interface is that electrochemically generated species may rapidly be involved in the interphase transfer process without at all extended diffusion distances and times for migration to the interface. This may be especially useful where electrochemically generated species are unstable or subject to side reactions within one of the fluid phases, but stabilised or rapidly taken up into a useful product within the other.

Figure 7A:
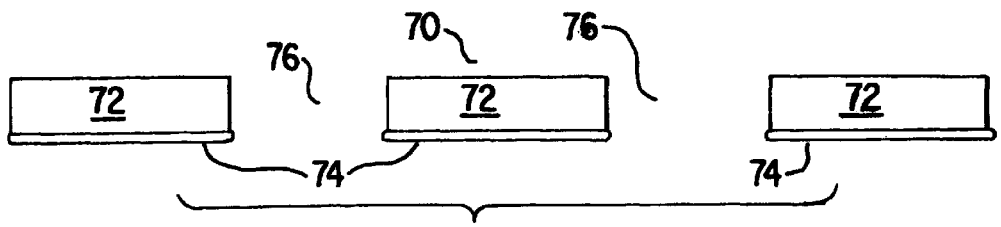
FIG. 7a–c are schematic views of apertures in sheets incorporating forms of electrode structures.

Referring now to FIG. 7 arrangements are shown embodying some of the above considerations and having conductive electrode materials deposited on the foraminous sheet. In FIG. 7a a foraminous sheet 70 has a substrate 72 having deposited on one surface electrode material 74 for interacting with or monitoring the immiscible fluid on that side of the sheet, with apertures 76 therein. The dimensions of the substrate and aperture are as indicated with reference to FIG. 1.

Figure 7B:
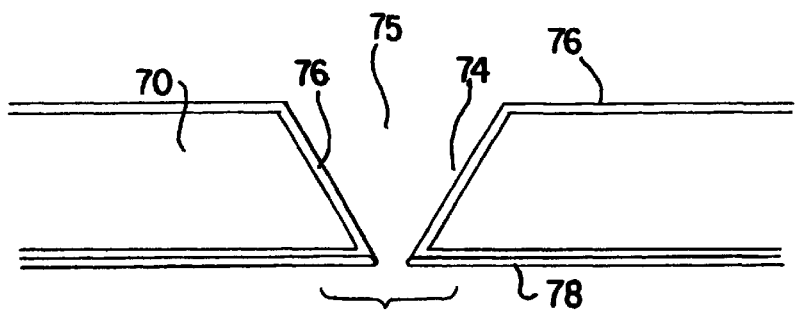

In FIG. 7b sheet 70 is formed from a sheet of silicon having tapered apertures 75 formed by a method as described above with reference to FIG. 4 and having on both sides of the silicon sheet and upon the walls of the aperture 75, a layer 76 of silicon nitride $Si_3N_4$, about 1 micrometer thick. On the lower surface of film 76 is deposited a metal layer 78 which serves as an electrode.

Figure 7C:
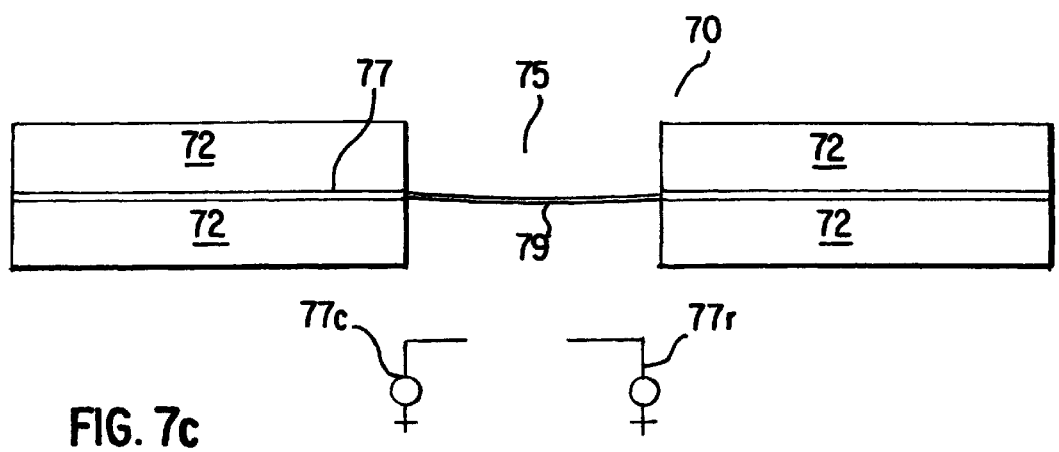

In FIG. 7c an arrangement is shown wherein the sheet 70 comprises first and third layers 72 of insulative material having a second thin layer 77 disposed therebetween of a metal or conductive carbon. An interface 79 is naturally located within aperture 75 adjacent metal layer 77, because of the different surface properties of the material, and the electrode serves to monitor or influence the interface 79. In FIG. 7c, counter and reference electrodes 77R, 77C are schematically indicated. These may be incorporated in the walls of fluid flow paths (not shown).

Figure 8:
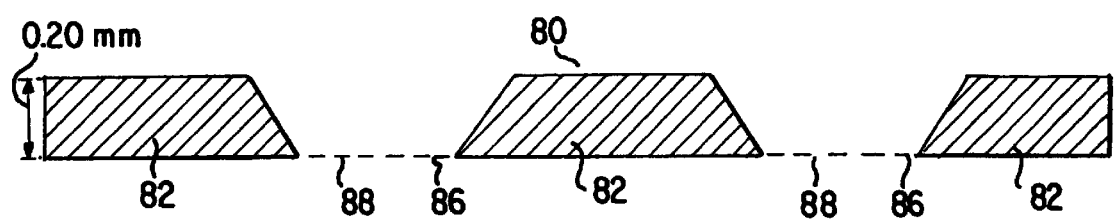
FIG. 8 is a schematic view of an embodiment of the invention incorporated in a three-dimensional structure.

Referring now to FIG. 8, this shows a 3 dimensional structure in which the foraminous sheet is incorporated. The structure comprises a silicon sheet, 200 micrometers wide, 80, etched to provide bars 82, quadrilateral in cross section and extending normal to the plane of the sheet, for providing support to a very thin layer of silicon 86, 10 microns in width, defining a series of foraminous sheet sections and having etched therein apertures 88 for defining interface regions. The bars 82 serve to support the thin sheet sections 86, and rest against the walls of the surrounding fluid flow channels (not shown).

We claim:

1. Apparatus for carrying out a diffusive transfer process between first and second immiscible fluids, comprising:
   first and second fluid flow paths for respective first and second fluids,
   a foraminous sheet means having apertures, said first and second fluid flow paths disposed on opposite sides of said foraminous sheet means,
   wherein an interface between the fluids is formed in use at or in each aperture,
   wherein a height of each of the apertures, as measured perpendicular both to a direction of fluid flow and to a thickness of the sheet means, is no more than 200 micrometers,
   wherein each aperture is formed to permit fluid to flow into the aperture without interfering with fluid flow out of the aperture thereby to permit a significant component of fluid flow of each fluid immediately adjacent the interface, the flow paths, sheet means and apertures being constructed and arranged such that the flow of the fluids is essentially laminar in the region of the sheet means, and
   wherein outside of a region defined by the sheet means, the first and second flow paths are separated to permit the respective first and second fluids to flow into and out of said region without mixing.

2. Apparatus according to claim 1, wherein inner walls of each aperture are essentially parallel to the width of the sheet means, and the aspect ratio of the width of each aperture across the thickness of the sheet means to the height of the aperture is less than or equal to one, such as to provide the capability of a significant component of fluid flow of each fluid immediately adjacent the interface.

3. Apparatus according to claim 1, wherein the walls of each aperture are tapered in the direction of fluid flow such as to permit fluid to flow into the aperture to the interface and fluid to flow from the interface out of the aperture thereby to permit a significant component of fluid flow of fluid immediately adjacent the interface.

4. Apparatus according to claim 3, wherein the walls of each aperture taper inwardly from each end to provide a region of minimum aperture height in a central region of the aperture.

5. Apparatus according to claim 1, wherein said height is between 1 and 30 micrometers.

6. Apparatus according to claim 1, wherein the width of the first and/or the second fluid path in the region of the sheet means and normal thereto is between 10 and 500 micrometers.

7. Apparatus according to claim 1, wherein the width of the first and/or the second fluid flow path in the region of the sheet means and normal thereto is less than a predetermined value, determined according to the following inequality:

$$l^2 < D.t.x^{-1}$$

wherein D is the diffusion constant for the respective fluid, t is the time of residence of the respective fluid in the region of the sheet means between 0.1 and 100 seconds, and x is a constant having a value of 0.005 or more.

8. Apparatus according to claim 7, wherein x has a value of 0.01 or more.

9. Apparatus according to claim 7, wherein x has a value of 0.1 or more.

10. Apparatus according to claim 1, including a third fluid flow path for a third fluid and a second sheet means through which the third fluid flow path communicates with the first or second flow paths, the third fluid being immiscible with the respective first or second fluid.

11. Apparatus according to claim 1, wherein the sheet means is formed or incorporated in a three-dimensional structure.

12. Apparatus according to claim 11, wherein said structure includes a series of block members separated by sheet sections constituting said sheet means, the block members forming a support for said sheet sections.

13. Apparatus according to claim 12, wherein the sheet means is formed from first and second sheet layers, one layer having different surface properties or electrical conductivity or other bulk property from the second layer.

14. Apparatus according to claim 13, wherein the first layer is hydrophilic and the second layer hydrophobic, or the first layer electrically insulating, and the second layer electrically conductive.

15. Apparatus according to claim 13, including a third layer, with the second layer interposed between the first and third layers.

16. Apparatus according to claim 1, wherein the sheet means is formed as a mesh, perforated sheet, or porous membrane.

17. Apparatus according to claim 16, wherein the sheet is formed from a solid plane sheet of material etched to provide spaced apertures.

18. Apparatus according to claim 1, wherein the apertures are extended in the direction of flow within the flow paths of fluid into and out of the apertures.

19. Apparatus according to claim 1, wherein the sheet means includes electrode means for monitoring or influencing the first and second fluids, and including counter and/or reference electrode means.

20. A method of carrying out a process of diffusive transfer of an entity from a first fluid to a second fluid immiscible with the first, the method comprising the steps of:

providing a foraminous sheet means having apertures and, on opposite sides and first and second flow paths communicating with one another across said foraminous sheet means having apertures, a height of each of the apertures in the sheet means being no more than 200 micrometers as measured at an interface position in a direction perpendicular both to a direction of fluid flow and to a width of the sheet means, each aperture being formed to permit fluid to flow into the aperture without interfering with fluid flow out of the aperture, flowing the first and second fluids through the respective first and second flow paths such that, at least in a region of the sheet means, the flow of the fluids is essentially laminar and stable interfaces are formed at or in the apertures of the sheet means at said interface position, with a significant component of fluid flow of each fluid immediately adjacent the interface, permitting diffusive transfer of at least 1% of a total amount of said entity that may be transferred, and flowing the fluids towards and away from the region of the sheet means in their respective flow paths without mixing of the fluids.

21. A method according to claim 20, wherein the inner walls of each aperture are essentially parallel to the width of the sheet means, and an aspect ratio of the width of the aperture across the thickness of the sheet means to the height of the aperture is less than or equal to one, such that a significant component of fluid flow of each fluid occurs immediately adjacent the interface.

22. A method according to claim 20, wherein the walls of each aperture are tapered in the direction of fluid flow such that fluid to flows into the aperture to the interface and fluid flows from the interface out of the aperture, with a significant component of fluid flow of fluid immediately adjacent the interface.

23. A method according to claim 20, and further comprising the step of having said height between 1 and 30 micrometers.

24. A method according to claim 20, and further comprising the step of having the width of the first and/or the second fluid flow path in the region of the sheet means and normal thereto between 10 and 500 micrometers.

25. A method according to claim 20, and further comprising the step of having the width (l) of the first and/or the second fluid flow path in the region of the sheet means and normal thereto be less than a predetermined value, determined according to the following inequality:

$$l^2 < D.t.x.^{-1}$$

wherein D is the diffusion constant for the respective fluid, t is the time of residence of the respective fluid in the region of the sheet means, and x is a constant having a value of 0.005 or more.

26. A method according to claim 25, wherein x has a value of 0.01 or more.

27. A method according to claim 25, wherein x has a value of 0.1 or more.

28. A method according to claim 20, including providing a third fluid flow path carrying a third fluid and a second sheet means through which the third fluid flow path communicates with the first or second flow paths, the third fluid being immiscible with the respective first or second fluid.

29. A method according to claim 20, wherein the apertures are extended in the direction of flow within the flow paths of fluid into and out of the apertures.

30. A method according to claim 20, including monitoring or influencing the first and second fluids, by means of electrode means and counter and/or reference electrode means.

* * * * *